US011021684B2

(12) United States Patent
Xiang et al.

(10) Patent No.: US 11,021,684 B2
(45) Date of Patent: Jun. 1, 2021

(54) **HIGH-QUALITY SEAWATER *SPIRULINA* STRAIN OBTAINED BY SPACE-BREEDING AND USE THEREOF**

(71) Applicants: SOUTH CHINA SEA INSTITUTE OF OCEANOLOGY, CHINESE ACADEMY OF SCIENCES, Guangzhou (CN); GUANGZHOU KENENG COSMETICS RESEARCH CO., LTD., Guangzhou (CN)

(72) Inventors: Wenzhou Xiang, Guangzhou (CN); Li Tan, Guangzhou (CN); Tao Li, Guangzhou (CN); Hualian Wu, Guangzhou (CN); Jiayi Wu, Guangzhou (CN); Zishuo Chen, Guangzhou (CN); Dehai Liu, Guangzhou (CN); Dengliang Yang, Guangzhou (CN); Shengjie Lin, Guangzhou (CN); Weijie Zhang, Guangzhou (CN); Chubiao Zhang, Guangzhou (CN); Hao Chen, Guangzhou (CN)

(73) Assignees: SOUTH CHINA SEA INSTITUTE OF OCEANOLOGY, CHINESE ACADEMY OF SCIENCES, Guangzhou (CN); GUANGZHOU KENENG COSMETICS RESEARCH CO., LTD., Guangzhou (CN)

( * ) Notice: Subject to any disclaimer, the term of this patent is extended or adjusted under 35 U.S.C. 154(b) by 0 days.

(21) Appl. No.: 16/608,867

(22) PCT Filed: Dec. 26, 2018

(86) PCT No.: PCT/CN2018/123727
§ 371 (c)(1),
(2) Date: Oct. 28, 2019

(87) PCT Pub. No.: WO2019/129021
PCT Pub. Date: Jul. 4, 2019

(65) Prior Publication Data
US 2020/0095538 A1  Mar. 26, 2020

(30) Foreign Application Priority Data
Dec. 28, 2017  (CN) .......................... 201711461143.2

(51) Int. Cl.
| | |
|---|---|
| *C12N 1/20* | (2006.01) |
| *C07K 14/795* | (2006.01) |
| *C12P 5/00* | (2006.01) |
| *C12P 19/04* | (2006.01) |
| *C12P 21/00* | (2006.01) |
| *C12R 1/01* | (2006.01) |

(52) U.S. Cl.
CPC .............. *C12N 1/20* (2013.01); *C07K 14/795* (2013.01); *C12P 5/005* (2013.01); *C12P 19/04* (2013.01); *C12P 21/00* (2013.01); *C12R 1/01* (2013.01)

(58) Field of Classification Search
CPC ......... C12N 1/20; C07K 14/795; C12P 5/005; C12P 19/04; C12P 21/00; C12R 1/01
USPC ........................................................ 435/243
See application file for complete search history.

(56) References Cited

U.S. PATENT DOCUMENTS 6,579,714 B1 * 6/2003 Hirabayashi ........... C12M 21/02
435/101

FOREIGN PATENT DOCUMENTS

| | | | |
|---|---|---|---|
| CN | 102041254 | A | 5/2011 |
| CN | 102041254 | * | 9/2012 |
| CN | 102899253 | A | 1/2013 |
| CN | 102911872 | A | 2/2013 |
| CN | 104894019 | A | 9/2015 |
| CN | 108265014 | A | 7/2018 |
| MD | 4492 | B1 | 6/2017 |

OTHER PUBLICATIONS

Murugan et al., Cultivation of two species of Spirulina (*Spirulina platensis* and *Spirulina platensis* var lonar) on sea water medium and extraction of C-phycocyanin, European Journal of Experimental Biology, vol. 4, No. 2, (2014), pp. 93-97.*
Sandeep et al., Cultivation of Spirulina (Arthrospira) platensis in low cost seawater based medium for extraction of value added pigments, Indian Journal of Geo-Marine Sciences, vol. 44, No. 3, (Mar. 2015), pp. 384-393.*
Wang Weibu, et. al, The breeding of spirulina platensis mutans with good quality and high yield induced by space flight, South China Fisheries Science, Dec. 2007, pp. 34-39, vol. 3, No. 6.
Chen Cheng-Hao, et. al, Evaluation on Growth and Biochemical Properties of Eight Strains of Marine Microalgae *Nannochloris* sp., Biotechnology Bulletin, 2016, pp. 231-237, 32(6).
Liang Jingle, et. al, Space-flight Mutation of Streptomyces gilvosporeus for Enhancing Natamycin Production, Chinese Journal of Chemical Engineering, 2007, pp. 720-724, 15(5).

* cited by examiner

*Primary Examiner* — Jennifer M. H. Tichy
(74) *Attorney, Agent, or Firm* — Bayramoglu Law Offices LLC

(57) ABSTRACT

A space-bred seawater *Spirulina* H11 strain. The strain exhibits high growth rate, capacity of simultaneously accumulating high contents of phycocyanin, *Spirulina* polysaccharides and β-carotene, and excellent adaptability to outdoor environment, thus can be used to produce high-quality *Spirulina* powders, phycocyanin, *Spirulina* polysaccharides, and β-carotene-rich *Spirulina* oil.

2 Claims, 3 Drawing Sheets

HIGH-QUALITY SEAWATER *SPIRULINA* STRAIN OBTAINED BY SPACE-BREEDING AND USE THEREOF

CROSS REFERENCE TO THE RELATED APPLICATIONS

This application is the national phase of International Application No. PCT/CN2018/123727, filed on Dec. 26, 2018, which is based upon and claims priority to Chinese Patent Application No. CN201711461143.2, filed on Dec. 28, 2017, the entire contents of which are incorporated herein by reference.

TECHNICAL FIELD

The present invention relates to the field of *Spirulina* cultivation, and particularly relates to a high-quality seawater *Spirulina* strain obtained by space-breeding and use thereof.

BACKGROUND

*Spirulina* are a group of prokaryotic algae classified under phylum Cyanobacteria, order Oscillatoriales, family Oscillatoriaceae and genus *Spirulina*. They have many physiological activities such as anti-HIV, anti-tumor, anti-oxidation, anti-radiation, anti-aging, improving gastrointestinal function, and lowering blood fat, and thus they have been internationally recognized as super-nutrition and health-care foods.

*Spirulina* contain 60% of proteins and other rich and unique bioactive substances, such as γ-linolenic acid, phycocyanin, β-carotene, inositol, *Spirulina* polysaccharides, vitamin B12, and minerals. Among the bioactive substances, phycocyanin, *Spirulina* polysaccharides, and high β-carotene *Spirulina* oil are attracting much attention. Phycocyanin is a special, naturally-occurred blue pigment protein, which has physiological activities such as anti-cancer, anti-tumor, anti-oxidation, free radical scavenging, and anti-allergy, and can be used as a natural pigment, fluorescent probe, medicine, health-care product and food. *Spirulina* polysaccharides are unique active ingredients from *Spirulina*, which have activities such as enhancing immunity, anti-radiation, anti-aging, lowering blood sugar, anti-fatigue, and anti-tumor. *Spirulina* oil rich in β-carotene has functions such as anti-oxidant, anti-inflammatory, anti-cancer, immunomodulatory, and coloring, and thus has great development prospects.

China is the world's largest producer of *Spirulina*. At present there are more than 100 companies that produce *Spirulina*, mainly distributed in Yunnan, Hainan, Jiangxi, Guangxi and Fujian. After 20 years of rapid development of China's *Spirulina* industry, the entire industrial chain is facing many serious problems at present. (1) It is a homogeneous market that most of the *Spirulina*-producing companies are very similar in a few respects such as their techniques, algae species and sales channels. These companies are in the same niche in the entire industrial chain, and thus the competition is fierce. (2) Value of the products is underestimated. *Spirulina*-producing companies produce *Spirulina* powders as the end products, most of which are exported to foreign countries, and thus the profit margin is largely reduced. (3) There are very few companies that further process *Spirulina*, and thus the active substances such as phycocyanin and *Spirulina* polysaccharides have not been effectively exploited. (4) The products have very limited application that most of the *Spirulina* products are sold in the form of health-care products, thus there is only small market space.

In order to solve the problems of the *Spirulina* industry, many companies and research institutes in China have focused on the following two aspects: (1) Improving the quality of *Spirulina* powders so as to obtain more profits. (2) Developing further-processed products of *Spirulina* and extracting the active substances such as *Spirulina* polysaccharides, phycocyanin and *Spirulina* oil, so as to increase the added value of *Spirulina*. However, there has not been much breakthrough in the industry transformation in China. At present in China, only a few companies produce phycocyanin, while there are no companies producing *Spirulina* polysaccharides or *Spirulina* oil. Technical bottlenecks in further-processing of *Spirulina* include: (1) Lack of high-performance *Spirulina* strains makes it impossible to produce *Spirulina* containing high contents of phycocyanin, *Spirulina* polysaccharides and β-carotene. (2) Low growth rate of *Spirulina* increases the cost of raw materials.

Space-breeding of microalgae is a more efficient artificial breeding method, in which genetic variation of microalgae is induced, under the mutagenic effect of cosmic radiation, microgravity or complex electromagnetic environment, to obtain a large amount of mutant strains, and then people may select for strains with high growth rates, high biomass contents, stable genetic traits and development values from the mutant strains. Compared with traditional breeding technologies, the biggest advantages of space mutation breeding include high mutation probability, wide variation range and short breeding period, making it possible to produce high-quality germplasm resources in a relatively short period. The seawater *Spirulina* strain provided by the present invention is obtained by space-breeding and multiple selections. The strain has a high growth rate and can simultaneously accumulate high contents of phycocyanin, *Spirulina* polysaccharides and β-carotene, thus it has a high development value.

Among the disclosed patents relative to *Spirulina*, none of them involves the protection of *Spirulina* species. We found some patents on improving the yield of *Spirulina* biomass and contents of active substances by modifying the cultivation conditions, typically comprising the followings:

(1) A method for simultaneously improving the yield of *Spirulina* biomass and polysaccharides (CN 201210318629.1). The invention causes the *Spirulina* to simultaneously accumulate biomass and polysaccharides by adjusting the addition of nutrient salts, which solves the problem that *Spirulina* are generally unable to simultaneously accumulate biomass and polysaccharides, and thus realizes rapid and efficient production of *Spirulina* polysaccharides. As *Spirulina* are usually cultivated in outdoor raceway ponds while outdoor cultivation will be affected by various weather conditions, there will be many uncertainty factors when scaling up from indoor evaluation to outdoor cultivation. Moreover, since the technology involves the adjusting of nutrient salts, it will require more labor and thus the cost is increased.

(2) A method for selective breeding of *Spirulina* (CN 201510280488.2). The invention discloses a method for selective breeding of *Spirulina*. The invention replaces the rough selection method using filtration mesh with a precise selection method using capillary tubes, so as to remove undesirable *Spirulina* individuals by single cell screening and obtain *Spirulina* species with high purity, high quality and high growth rate. The *Spirulina* yield has been increased by 30% to 50%, and the product quality has been further improved. The patent technique has limitations that it is impossible for an algae strain obtained by the screening method to exhibit a performance that the original strain does not exhibit.

(3) Method for improving carbohydrate contents in *Spirulina* cells (CN 201210418828.X). The invention provides a method for improving carbohydrate and polysaccharide contents in *Spirulina* cells, wherein a *Spirulina* solution is added to an algae pond and let stand until the *Spirulina* cells are suspended over the surface of the algae pond, which is then placed under intensive light, causing most of *Spirulina* cells sink to the bottom, and then the *Spirulina* cells at the bottom are collected as raw materials for extracting *Spirulina* polysaccharides. The *Spirulina* carbohydrate content can be increased by over 16 percentages, largely improving the efficiency of *Spirulina* cultivation, reducing the cost and significantly improving economic efficiency. However, the patent technique has problems when scaled up.

(4) Method for breeding space *Spirulina* (CN 200910181145.5). The method of the invention comprises the steps of space mutagenesis, separation and screening, and repeated selective breeding. The *Spirulina* mutants obtained by this method are superior to common species in length, width, helical pitch, helical width, helical number, and nutrient contents. The patent claims the protection of a technique for space-breeding and screening of high-quality *Spirulina* strains; however, it does not involve any strain with a specific characteristic, thus will not conflict with the present invention.

Through the analysis of the above patents, it is suggested that there are not any patent claiming the protection of a *Spirulina* strain. In respect to the improvement of phycocyanin and *Spirulina* polysaccharide contents, the disclosed techniques realize the improvement by modifying cultivation conditions or processes; however, many factors are to be considered when scaling up the above techniques, making it difficult to scale up and thus they are infeasible.

*Spirulina* are able to accumulate a plurality of bioactive substances, among which *Spirulina* polysaccharides, phycocyanin, and *Spirulina* oil rich in β-carotene are attracting much attention. At present, the strains used by *Spirulina* companies in China and abroad are able to produce the three active substances mentioned above, but the produced algae powders or algae slurries are still inapplicable for large-scale extraction of the three active substances, mainly due to the following reasons:

(1) The contents of polysaccharides, phycocyanin and β-carotene in *Spirulina* powders or slurries are relatively low, failing to meet the requirements of raw materials for extraction, resulting in high extraction cost and low yield. In view of this problem, the present invention provides a seawater *Spirulina* strain which is obtained by space-breeding and multiple selections, wherein the strain is able to accumulate high contents of *Spirulina* polysaccharides, phycocyanin and β-carotene, thus meeting the requirements on the contents of active substances for further-processing extraction.

(2) The strains used by the *Spirulina*-cultivating companies have low growth rate and are unable to give high biomass contents. In view of this problem, the present invention provides a *Spirulina* strain that has a relatively high growth rate, is able to accumulate high contents of phycocyanin, *Spirulina* polysaccharides and β-carotene, and thus can be used as a substitute of the currently used *Spirulina* strains.

(3) *Spirulina* cultivation is high in cost, and has the issues of easily contaminating other blue-green algae and heavy metals enrichment.

SUMMARY

In view of the above problems, the present invention provides a seawater *Spirulina* strain obtained by space-breeding, a *Spirulina platensis* $H_{11}$ strain. The strain exhibits high growth rate, capacity of simultaneously accumulating high contents of phycocyanin, *Spirulina* polysaccharides and β-carotene, and excellent adaptability to outdoor environment, thus can be used to produce high-quality *Spirulina* powders, phycocyanin, *Spirulina* polysaccharides, and β-carotene-rich *Spirulina* oil, showing high development potential.

The *Spirulina platensis* $H_{11}$ strain of the present invention, i.e., *Spirulina platensis* SCSIO-44012-H11, has been deposited with the China Center for Type Culture Collection (CCTCC), located at Wuchang, Wuhan, China, on Dec. 8, 2017, and has been assigned an accession number: CCTCC M 2017772.

Cultivation conditions for the seawater *Spirulina platensis* $H_{11}$ strain of the present invention include the use of natural freshwater or seawater added with four elements including carbon, nitrogen, phosphorus, and iron. A salinity of the water is 0‰ to 50‰. The element nitrogen can be introduced in the form of sodium nitrate, potassium nitrate, carbamide, ammonium bicarbonate, ammonium carbonate, or ammonia, at a concentration of 0.1 mM to 20 mM. The element carbon can be introduced in the form of carbon dioxide, sodium carbonate, or sodium bicarbonate, at a concentration of 0.1 mM to 250 mM. The element phosphorus can be introduced in the form of sodium dihydrogen phosphate, potassium dihydrogen phosphate, disodium hydrogen phosphate, dipotassium hydrogen phosphate, or phosphoric acid, at a concentration of 0.1 mM to 20 mM. The element iron can be introduced in the form of ferrous sulfate or ferric chloride, at a concentration of 10 μM to 50 μM.

Under normal cultivation conditions, the seawater *Spirulina platensis* $H_{11}$ strain of the present invention can produce 0.885 g/L of biomass, 16.24 g/100 g of phycocyanin, 0.136 g/100 g of β-carotene, and 24.8 g/100 g *Spirulina* polysaccharides, much higher than those produced by the original unmutated seawater *Spirulina* strain. Thus, the seawater *Spirulina platensis* $H_{11}$ strain of the present invention can be used in a large-scale production, so as to obtain *Spirulina* biomass containing higher contents of phycocyanin, *Spirulina* polysaccharides and β-carotene, and reduce the cost of *Spirulina* cultivation; the *Spirulina* biomass can be used in the extraction of *Spirulina* polysaccharides, β-carotene-rich *Spirulina* oil and phycocyanin.

Accordingly, the second object of the present invention is to provide the use of the seawater *Spirulina platensis* $H_{11}$ strain in producing phycocyanin, *Spirulina* polysaccharides, β-carotene and *Spirulina* powders.

The seawater *Spirulina platensis* $H_{11}$ strain can simultaneously contain high contents of phycocyanin, *Spirulina* polysaccharides and β-carotene, and the high-quality *Spirulina* powders can be used in the fields of feed additives, health-care products, foods, aquafeeds, and cosmetics.

The seawater *Spirulina platensis* $H_{11}$ strain of the present invention can be harvested with a low cost by means of filtration.

The seawater *Spirulina platensis* $H_{11}$ strain of the present invention can be cultivated under outdoor and indoor conditions, with a light intensity of 50 to 5000 μmol photons/$m^2$s.

The space-bred seawater *Spirulina* $H_{11}$ strain provided by the present invention has the following advantages:

(1) The strain of the present invention can simultaneously accumulate high contents of *Spirulina* polysaccharides, phycocyanin and β-carotene, thus can be used to produce high-quality *Spirulina* powders meeting the requirements on the contents of active substances for extraction.

(2) The strain of the present invention exhibits high growth rate and the capacity of high content of biomass, significantly superior to existing strains, thus can be used as a substitute of the currently used strains.

(3) The strain of the present invention can be cultivated with natural seawater, wherein the growth requirements thereof can be met by merely adding four elements, carbon, nitrogen, phosphorus, and iron, into the natural seawater, which largely reduce the use of fertilizer and cut the cultivation cost. Moreover, seawater cultivation can avoid the contamination of microcystins and other heavy metals to a certain extent.

Thus, the space-bred seawater *Spirulina* $H_{11}$ strain provided by the present invention exhibits high growth rate, capacity of simultaneously accumulating high contents of phycocyanin, *Spirulina* polysaccharides and β-carotene, and excellent adaptability to outdoor environment, thus can be used to produce high-quality *Spirulina* powders, phycocyanin, *Spirulina* polysaccharides, and β-carotene-rich *Spirulina* oil, showing high development potential.

The *Spirulina platensis* SCSIO-44012-H11 has been deposited with the China Center for Type Culture Collection (CCTCC), located at Wuchang, Wuhan, China, on Dec. 8, 2017, and has been assigned the accession number: CCTCC M 2017772.

DETAILED DESCRIPTION OF THE EMBODIMENTS

In order to allow those skilled in the art better understand the technical solutions of the present invention, the present invention will be further described in detail below with reference to specific embodiments.

Embodiment 1

1. Selective Breeding of High-Quality Space Seawater *Spirulina* $H_{11}$ Strain (1) *Spirulina platensis* strains which had once been cultivated in a space station were cultivated through an inoculum expansion process in 50-mL Erlenmeyer flasks. After the strains were grown to a certain density, a preliminary screening was carried out.

(2) After isolating single filaments, the single-cell mutants were transferred to sterile 96-well plates and cultivated under light conditions for about 10 days. Color changes in the wells were monitored, and changes in $OD_{750}$ values were determined with a microplate reader.

(3) Strains with significantly higher growth rates in the 96-well plates were cultivated through an inoculum expansion process in 50-mL Erlenmeyer flasks, and then evaluation of the mutants was carried out with 500-mL Erlenmeyer flasks.

Figure 2:
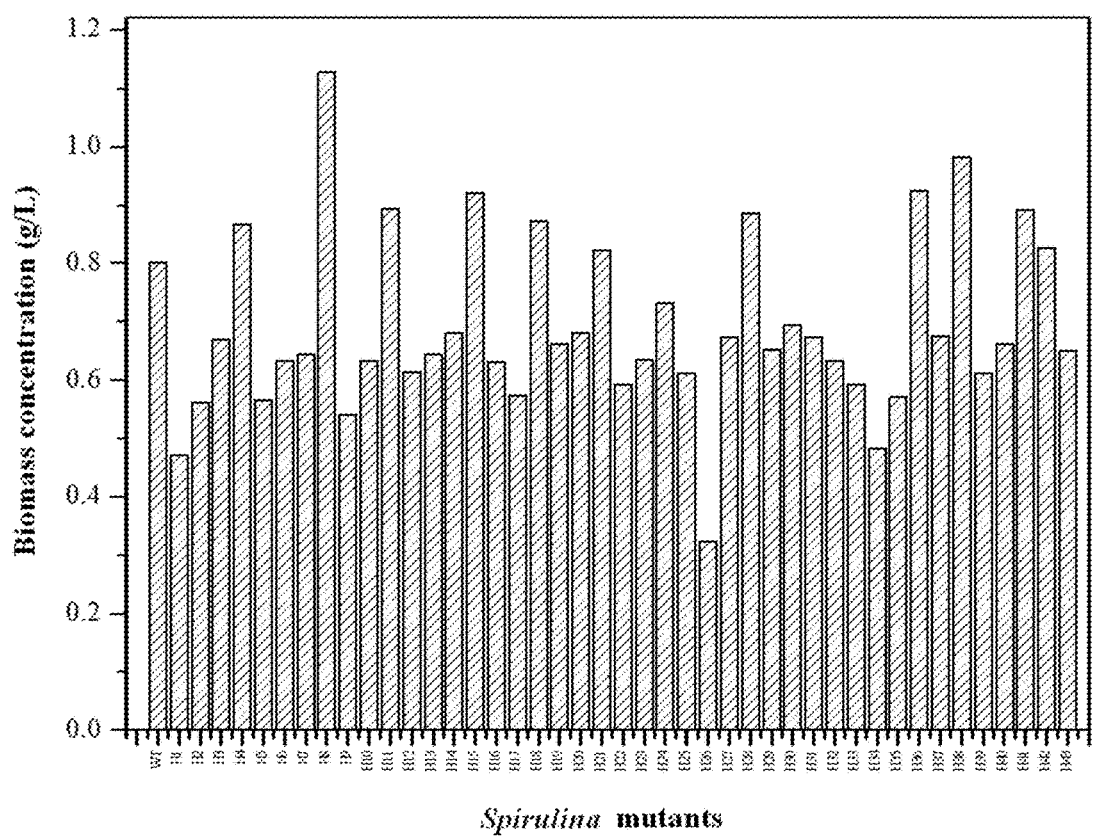
FIG. 2 shows the screening of the seawater *Spirulina* $H_{11}$ strain.

(4) The seawater *Spirulina* $H_{11}$ strain, which exhibited a better performance, was selected by measuring biomass concentration, polysaccharide content, phycocyanin content and β-carotene content in the Erlenmeyer flasks (FIG. 2).

Figure 1:
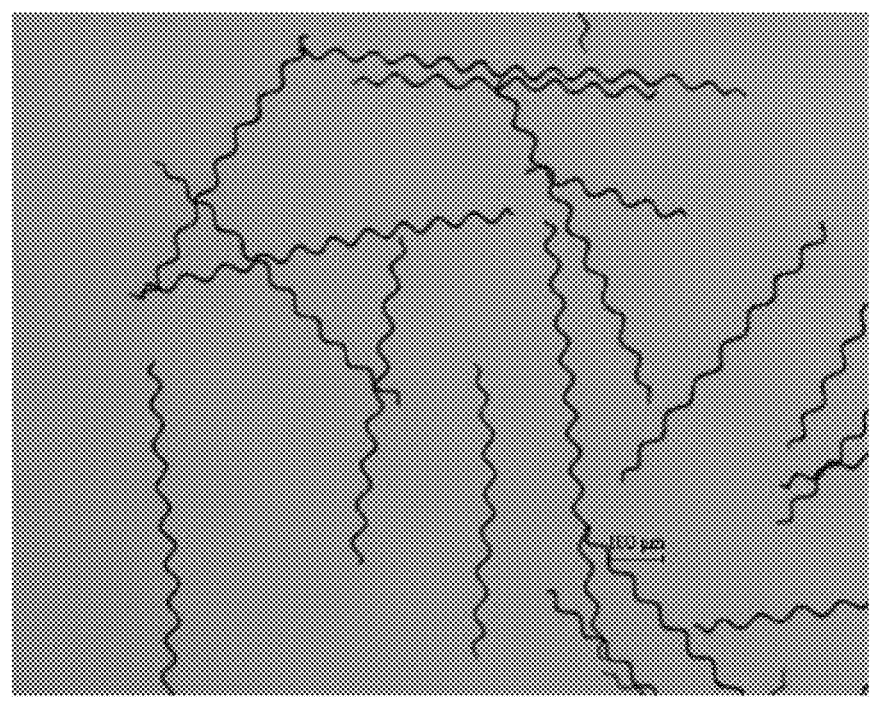
FIG. 1 shows cellular morphology of the seawater *Spirulina*.

Morphology of the seawater *Spirulina* $H_{11}$ strain (*Spirulina platensis*) (FIG. 1): Cylindrical, helical and unbranched filaments, a filament diameter of 5 to 10 μm, regularly helical, a helical number of 2 to 15, a length of 200 to 500 μm, no heterocyst or akinete, no gelatinous sheath or merely a thin sheath.

The seawater *Spirulina* (*Spirulina platensis*) $H_{11}$ strain (i.e., the *Spirulina platensis* SCSIO-44012-H11), has been deposited with the China Center for Type Culture Collection (CCTCC), located at Wuchang, Wuhan, China, on Dec. 8, 2017, and has been assigned the accession number: CCTCC M 2017772.

2. Obtaining Biomass from the Space Seawater *Spirulina* $H_{11}$ Strain

Culture medium: The medium was prepared by adding 5.0 g of $NaHCO_3$, 0.5 g of $NaNO_3$, 0.05 g of $K_2HPO_4$, and 0.01 g of $FeSO_4 \cdot 7H_2O$ into 1 L of natural seawater having a salinity of 25‰, mixing evenly and sterilizing.

Figure 3:
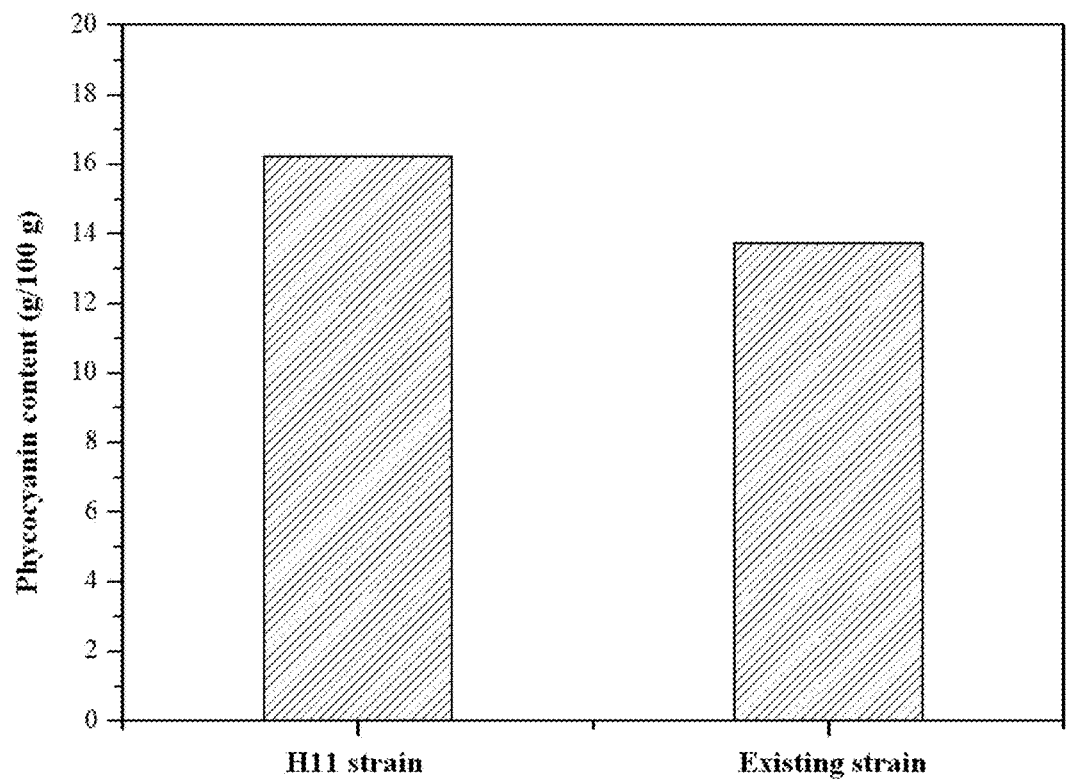
FIG. 3 shows the comparison in phycocyanin content between the seawater *Spirulina* $H_{11}$ strain and an existing unmutated wild *Spirulina* strain.
Figure 4:
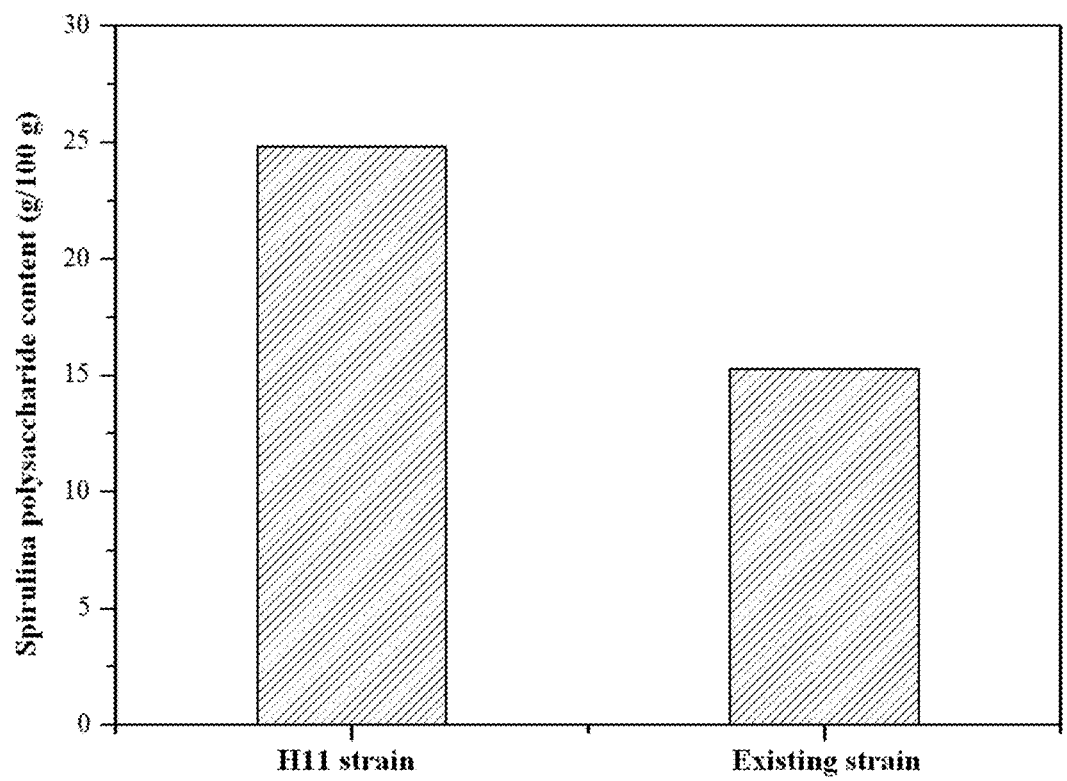
FIG. 4 shows the comparison in *Spirulina* polysaccharide content between the seawater *Spirulina* $H_{11}$ strain and an existing unmutated wild *Spirulina* strain.
Figure 5:
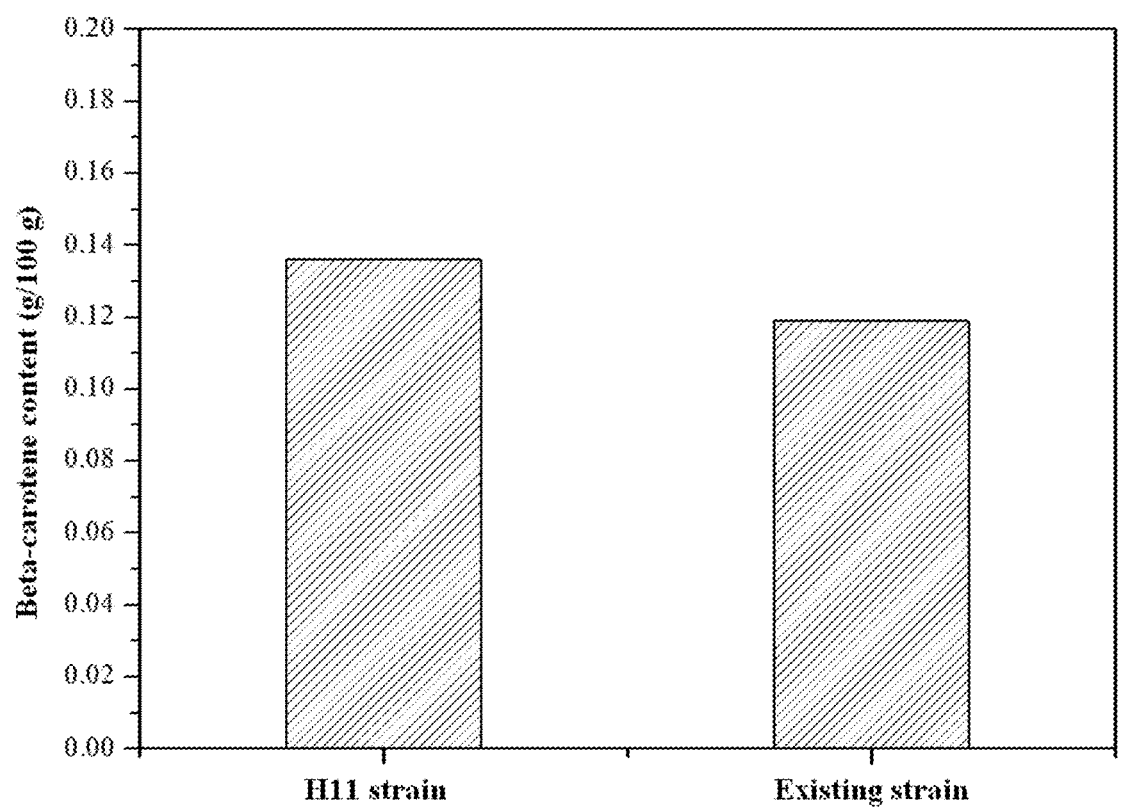
FIG. 5 shows the comparison in β-carotene content between the seawater *Spirulina* $H_{11}$ strain and an existing unmutated wild *Spirulina* strain.

The seawater *Spirulina* (*Spirulina platensis*) $H_{11}$ strain and an unmutated wild seawater *Spirulina* (*Spirulina platensis*) strain (control) were respectively inoculated into the medium at a same inoculum size, and cultivated for 10 days with a light intensity of 150 μmol photons/$m^2$s and a temperature of 25° C. 0.885 g/L of biomass was obtained from the seawater *Spirulina* (*Spirulina platensis*) $H_{11}$ strain of the present invention, with a phycocyanin content of 16.24 g/100 g, a β-carotene content of 0.136 g/100 g, and a *Spirulina* polysaccharide content of 24.8 g/100 g. 0.802 g/L of biomass was obtained from the original seawater *Spirulina* (*Spirulina platensis*) strain as the control (i.e., the existing strain in FIGS. 3, 4 and 5), with a phycocyanin content of 13.7 g/100 g, a β-carotene content of 0.119 g/100 g, and a *Spirulina* polysaccharide content of 15.3 g/100 g. See FIGS. 3, 4 and 5 for details.

After 30 cycles of subculture, the seawater *Spirulina* $H_{11}$ strain exhibited stable inheritance in the biomass concentration, high polysaccharide content, high phycocyanin content and high β-carotene content, which were far higher than those of the existing strain.

3. Composition Analysis of Polysaccharides of the Space Seawater *Spirulina* $H_{11}$ Strain Polysaccharide compositions in the *Spirulina* solutions which had been cultivated for 10 days in step 2 were analyzed. The results were as listed in Table 1. As can be seen from Table 1, the content of polysaccharides having a molecular weight of over 3500 Da was 21.28% of the dry weight of the seawater *Spirulina* $H_{11}$ strain, which was increased by 76% as compared with the unmutated wild *Spirulina* strain, indicating high development potential.

TABLE 1

|  | Over 3500 Da (% dry weight) | Below 3500 Da (% dry weight) | Water-insoluble polysaccharides (% dry weight) |
|---|---|---|---|
| $H_{11}$ strain | 21.28 ± 0.34 | 1.71 ± 0.03 | 1.82 ± 0.04 |
| Existing strain | 12.07 ± 0.15 | 1.78 ± 0.01 | 1.44 ± 0.01 |

Note:
"$H_{11}$ strain" refers to the seawater Spirulina $H_{11}$ strain, and "existing strain" refers to an existing unmutated wild Spirulina strain.

What is claimed is:

1. A method of using a *Spirulina platensis* $H_{11}$ strain with an accession number CCTCC M 2017772 in producing phycocyanin or *Spirulina* polysaccharides or β-carotene, comprising:

cultivating the *Spirulina platensis* $H_{11}$ strain in a medium to produce biomass, wherein the medium is prepared by adding 5.0 g of $NaHCO_3$, 0.5 g of $NaNO_3$, 0.05 g of $K_2HPO_4$, and 0.01 g of $FeSO_4.7H_2O$ into 1 L of natural seawater having a salinity of 25%; and extracting the phycocyanin or the *Spirulina* polysaccharides or the β-carotene from the biomass.

2. The method of claim 1, wherein the *Spirulina platensis* $H_{11}$ strain is cultivated in the medium with a light intensity of 150 μmol photons/m²s and a temperature of 25° C.

* * * * *